United States Patent [19]

Rosenthal et al.

[11] Patent Number: 5,565,210
[45] Date of Patent: * Oct. 15, 1996

[54] BIOABSORBABLE WOUND IMPLANT MATERIALS

[75] Inventors: Arthur L. Rosenthal, Arlington, Tex.; Nicholas D. Light, Doune; Paul W. Watt, Broomridge, both of United Kingdom

[73] Assignee: Johnson & Johnson Medical, Inc., Arlington, Tex.

[ * ] Notice: The portion of the term of this patent subsequent to Feb. 24, 2015, has been disclaimed.

[21] Appl. No.: 417,184

[22] Filed: Apr. 5, 1995

Related U.S. Application Data

[63] Continuation of Ser. No. 35,015, Mar. 22, 1993, abandoned.

[51] Int. Cl.⁶ .............................. A61F 2/02; A61K 47/36; A61K 47/38; A61K 47/42
[52] U.S. Cl. ............... 424/426; 424/423; 424/425; 514/773; 514/774; 514/777; 514/781; 514/953
[58] Field of Search ........................... 424/423, 425, 424/426; 514/773, 774, 777, 781, 953

[56] References Cited

U.S. PATENT DOCUMENTS

| | | | |
|---|---|---|---|
| 4,233,660 | 11/1990 | Luck et al. | 424/443 |
| 4,320,201 | 3/1982 | Berg et al. | 435/265 |
| 4,614,794 | 9/1986 | Easton et al. | 530/356 |

FOREIGN PATENT DOCUMENTS

| | | |
|---|---|---|
| 0167828 | 11/1986 | European Pat. Off. . |
| 0246638 | 11/1987 | European Pat. Off. . |
| 0274898 | 7/1988 | European Pat. Off. . |
| 0314109 | 5/1989 | European Pat. Off. . |
| 0403650 | 12/1990 | European Pat. Off. . |
| 2377205 | 1/1978 | France . |
| 4037931 | 5/1992 | Germany . |
| 3-23864 | 6/1989 | Japan . |
| 1144552 | 3/1969 | United Kingdom . |
| 2215209 | 9/1989 | United Kingdom . |
| W0854413 | 10/1985 | WIPO . |
| 9000060 | 1/1990 | WIPO . |
| W090/00060 | 1/1990 | WIPO . |

OTHER PUBLICATIONS

Collagen Sponge: Theory and Practice of Medical Applications; J. Biomed Mater. Res.; vol. 11, pp. 721–741 (1977), Milos Chvapil.

Design of an Artificial Skin. I. Basic Design Principles; J. Biomed. Res. vol. 14, p. 65–81 (1980), I. V. Yannas and John F. Burke.

*Primary Examiner*—Carlos Azpuru
*Attorney, Agent, or Firm*—Andrew C. Farmer

[57] ABSTRACT

Heteromorphic sponges are described which have matrix structures with oriented substructures added to facilitate cellular invasion. A sponge may be used as a wound implant by cutting it to the shape of a wound bed and placing therein. The matrix structure provides conduits which assist invasion of the sponge by cells which degrade the sponge and lay down new tissue to replace it. The incorporation of active agents in the matrix and/or substructures enhances wound healing.

15 Claims, No Drawings

BIOABSORBABLE WOUND IMPLANT MATERIALS

This is a continuation of application Ser. No. 08/035,015, filed Mar. 22, 1993 now abandoned.

The present invention relates to bioabsorbable wound implant materials, and more particularly to heteromorphic sponge materials containing an oriented substructure, which are suitable for use as implantable materials in wound repair.

Porous materials formed from synthetic and/or naturally occurring bioabsorbable materials have been used in the past as wound dressings or implants. The porous material provides structural support and a framework for tissue ingrowth while wound healing progresses. Preferably, the porous material is gradually absorbed as the tissue around the wound regenerates.

Typical bioabsorbable materials for use in the fabrication of porous wound dressings or implants include synthetic bioabsorbable polymers such as polylactic acid or polyglycolic acid, and also biopolymers such as the structural proteins and polysaccharides. The structural proteins include collagen, elastin, fibronectin, laminin and fibrin, as well as other proteins of the human connective tissue matrix. Of these, the most studied material has been collagen.

Collagen is the most abundant animal protein and the major protein of skin and connective tissue. A high degree of homology exists between the various types of collagen found in different animal species and human collagen. Accordingly, animal collagen types such as bovine collagen are useful because they exhibit very low immunogenicity when implanted into humans or used as topical dressings on human wounds.

Collagen may be prepared in a variety of physical forms including fibres, flakes, films or aqueous gels. Freeze drying an aqueous gel or an aqueous suspension of collagen may be used to produce a porous collagen sponge. Collagen sponges are described, for example, in Chvapil, J. Biomed. Mater. Res. 11 721–741 (1977). The use of collagen sponges and/or other freeze-dried biopolymer sponges as wound dressings or implant materials is disclosed, for example, in US-A-4614794 and US-A-4320201.

High molecular weight polysaccharides of the mammalian connective tissue matrix have also been used in various types of wound dressing or "synthetic skins". Yannas I. V. & Burke, J. F., J. Biomed. Mater. Res. 14 56–81 (1980) describe the use of such polysaccharides in wound dressings formed by freeze drying as sponges. High molecular weight polysaccharides include such molecules as chondroitin sulphate, hyaluronic acid and dermatan sulphate.

US-A-4614794 describes the use of other naturally occurring polysaccharide materials, especially of plant origin, in the dressing of wounds. These include, for example, alginates, chitosan, chitin, guar gum, and various plant gums.

Porous materials comprising more than one kind of bioabsorbable polymer have also been suggested for use as wound implants or wound dressings. For example:

GB-A-2215209 (Osmed Inc.) describes a biodegradable, osteogenic bone-graft substitute comprising: (a) a porous, rigid structure formed from a biodegradable polymer such as polylactic or polyglycolic acid; (b) a chemotactic substance such as hyaluronic acid, fibronectin or collagen dispersed in the interstices of the rigid structure, and (c) a biologically active or therapeutic substance such as bone morphogenetic protein. In use, the material is implanted into a bone defect. The material helps to restore functional architecture and mechanical integrity of the bone, initiate osteogenesis, and maintain the biological processes of bone growth while simultaneously being slowly bioabsorbed by the host organism.

JP-A-03023864 (Gunze KK) describes a reinforced collagen sponge for use as a filling material for biological tissue. The collagen sponge is reinforced by the addition of fibres of poly-(L-lactic acid). The resulting fibre-reinforced composite sponge is stronger than pure collagen or cross-linked collagen sponges, and is bioabsorbed more slowly in a host organism.

Implants made from biological, bioabsorbable components are normally intended to be invaded by the cells of the host or recipient of the implant. Cellular invasion of homogeneous sponge implants, however, is not necessarily achieved in the most efficient manner. The closed honeycomb nature of sponges presents a series of "walls" to cells invading the structure, each of which has to be breached before progress can continue. Cellular invasion is required by cells which can degrade the implant materials and by those which can lay down the tissue to replace the implant and thus repair any defect which the implant is intended to repair. Failure of either type of cell to invade the structure of the implant in an efficient manner prevents vascularisation which is required for new tissue to be able to sustain its life.

Furthermore, the porous bioabsorbable implants that have been suggested to date are all isotropic materials. That is to say, the structure and composition of the materials are uniform in all directions. This does not conform to the reality of wound healing, according to which vascularisation and tissue ingrowth into wounds are highly directional. For example, tissue ingrowth normally takes place from the edges of a skin wound, and not from the wound bed. For optimised wound healing the implant material should be anisotropic so as to allow rapid tissue ingrowth in the preferred wound healing direction while maintaining maximum structural stability in all other directions.

Accordingly, it is an object of the present invention to provide a porous bioabsorbable material that is suitable for use in the repair of full and partial thickness defects of the skin and defects or deficiencies of other soft tissues. In particular, it is an object of the present invention to provide a porous material that is readily invaded by cells of the host organism and that is anisotropic.

The present invention provides a bioabsorbable heteromorphic sponge comprising a matrix structure of sponge and at least one substructure, wherein the matrix and the substructure are formed of bioabsorbable materials and the substructure is oriented.

The term "heteromorphic" means that the sponges according to the present invention are structurally inhomogeneous due to the presence of the substructure in the sponge matrix. The sponges according to the present invention may also be chemically inhomogeneous if the substructure has a different chemical composition than the sponge matrix.

The substructure in the heteromorphic sponge according to the present invention is oriented. That is to say, the substructure is anisotropic and thereby defines preferred directions for cellular ingrowth into the sponge. The anisotropy is normally provided by the use of oriented flakes, films, fibres or the like to form the substructure.

The sponge is bioabsorbable in that it is capable of full degradation and resorption within a patient's body. The heteromorphic sponge is preferably used as a wound implant for example in partial or full thickness skin injury or in tissue insufficiency where soft tissues are required to be replaced.

Preferably, the matrix and the substructure are both formed from biodegradable biopolymer materials.

The matrix is preferably strong and resilient enough to resist collapse and may be cut and/or formed so as to conform to a wound shape so that it protects and/or fills a wound bed. It may, for example, be cut so as to fill the full depth of a wound or tissue deficient area.

A heteromorphic sponge which has been cut to shape can then be placed into a debrided wound bed. A wound which has a heteromorphic sponge implanted therein may then be dressed with a suitable dressing and healing allowed to take place. Regrowth of new tissue into the heteromorphic sponge enhances wound healing.

The heteromorphic sponge may allow wound fluid, oxygen and other gases to pass through the sponge and can be replaced by host tissues in such a way that healing is promoted and cosmetic damage minimised.

Preferably, the sponge matrix comprises one or more proteins or one or more polysaccharides, or a mixture of one or more proteins with one or more polysaccharides. In particularly preferred embodiments, the sponge matrix consists essentially of collagen. The collagen may be provided by harvesting it as a fibrous mass containing largely collagen types I and III from such animal sources as skin, tendon, intra-organ connective tissue and bone and from such species as cattle, sheep, pigs, chickens, turkeys, kangaroo, deer or other mammals.

The sponge matrix and substructures within the matrix may include all collagen types, tenascin, laminin, chondroitin sulphate, hyaluronic acid, dermatan sulphate, heparin sulphate, heparin, elastin, fibrin, fibronectin, vitronectin, dextran, or oxidised regenerated cellulose.

The substructures are non-randomly deposited, oriented substructures. They may be formed from material which is the same material as that of the matrix or may be formed from another material. The substructure may be films, flaked or otherwise broken films, fibres, fibre bundles or mixtures of these. The substructures may comprise materials which make up for tissue deficiency or which contain active agents which may control, enhance or encourage wound healing.

Oriented substructures within the matrix provide conduits or pathways for cells to follow, enabling them to invade into the body of the matrix of the heteromorphic sponge. Particularly preferred for this purpose are substructures which are elongate or flat and planar, such as films or film flakes, fibres or fibre bundles. The sponge component of the matrix thus has its homogeneous structure sufficiently interrupted by the substructures to facilitate cellular movement. Thus, endothelial cells and fibroblasts can migrate relatively rapidly in the matrix structure and begin, at an early stage after implantation, the process of degradation and renewal.

Preferably, at least 75% of the substructure is oriented within 30 degrees of a mean direction of orientation of the substructure. For example, where the substructure comprises fibres or fibre bundles, preferably at least 75% of the fibres are oriented within 30 degrees of the mean direction of orientation of the fibres. Where the substructure comprises flakes or films or other substantially planar fragments, coplanarity of the planar fragments is not required provided that the fragments of the substructure are sufficiently oriented to provide for anisotropic cellular ingrowth into the heteromorphic sponge. For example, the planar fragments could be organised like the cell walls of a honeycomb, defining one-dimensional channels for cellular ingrowth. In such a case, preferably at least 75% of the planar fragments intersect at an angle of 30 degrees or less with an axis running parallel to the channels. In an alternative arrangement, the planar fragments of the substructure are arranged in a substantially coplanar stack such that the heteromorphic sponge has a laminated structure. This arrangement provides two-dimensional planes for cellular ingrowth. Preferably, at least 75% of the planar fragments are oriented such that their perpendiculars are inclined at an angle of 30 degrees or less to the mean perpendicular direction.

More preferably, at least 75% of the substructure is oriented within 20 degrees of a mean direction of orientation of the substructure.

In another preferred embodiment the heteromorphic sponge may further include materials which are active in aiding in the healing process. Active molecules may include: antimicrobials to control infection; cytokines and growth factors to enhance healing; antibodies to specific wound components such as TGFβ to prevent contracture; collagen; peptides to act as chemotactic agents, angiogenic factors, hormones and enzymes; or pain killers.

The heteromorphic sponge may be formed by making a heterogeneous premix comprising the substructure material suspended in a gel, paste, slurry or emulsion of the matrix material which is then freeze dried.

The orientation of the substructure may be achieved in different ways. For example, the elements of the substructure such as films, fibres and the like may be laid down in an ordered fashion in a bath of the matrix gel, paste or slurry. Alternatively, the substructure may be an ordered structure such as a honeycomb of the substructure material which is then flooded with the matrix gel, paste or slurry. Spontaneous ordering of the substructure can also take place. For example, where flakes of the substructure material are stirred into a slurry as above and the mixture is allowed to stand before freeze drying, spontaneous ordering of the flakes is observed in the freeze-dried product. Spontaneous ordering of flakes and fibres also occurs when pastes or gels containing these substructures are extruded.

In a preferred method, fibrous collagen, pre-washed to remove the majority of non-collagenous components as described in US-A-4614794 or US-A-4320201 is suspended in clean deionised pyrogen free water and homogenised to a fine fibrous suspension by passage through a homogenising system. Suitable homogenising systems are described in US-A-4320201.

Homogenisation may be continued until a desired degree of fibre division is achieved. This results in a preferred fibre size of between 0.01 and 10 mm.

Preferably, homogenised collagen is acidified to cause it to swell to a premix or gel suitable for freeze drying. The acidifying step may use an organic acid such as formic, acetic, propionic, lactic, malonic, or dilute inorganic acids such as hydrochloric acid at a solids content of between 0.01% and 30% to a final pH of between 2 and 6. A preferred embodiment results in a pH of between 3.0 and 4.5.

Adding sub-components to the matrix which enhance the regrowth of tissues preferably produces a final concentration of between 0.01% and 50% of the dry weight of the material. The second components may then be mixed so as to disperse them throughout the body of the premix. Mixing usually comprises stirring and may further include adding cross-linking agents to stabilise the matrix.

A plasticiser such as glycerol or sorbitol may be added to a final concentration of between 0.1% and 5%, based on the dry weight of collagen, and mixed with the premix. Oil may also be added at this stage with adequate homogenisation. The resulting matrix may comprise a slurry, gel, paste, emulsion or suspension which may then be mixed quickly with a preformed, fabricated solid material of the substructure to form the heterogeneous mix desired. This is then preferably fully degassed, poured into trays and freeze dried.

The heteromorphic sponge can be freeze dried at its desired final thickness or dried as a block and cut to size and shape prior to packaging and sterilisation. Where a film is produced, this may be rolled onto tube carriers or pre-cut into lengths and stored flat. Films may also be made by pouring a slurry of collagen onto flat trays and drying in a stream of warm air at between 20° C. and 80° C.

Drugs or active agents which are required for incorporation into the heteromorphic sponges may be added to the sponge mixture or to the second components which will become substructures of the sponge before these are added to the premix for freeze drying.

The invention is now further described with reference to the following examples.

EXAMPLE 1 (Comparative Example)

An isomorphic single-component collagen sponge is prepared as follows.

An acetic acid suspension of collagen is prepared substantially as described above and in US-A-4614794. The suspension is adjusted to 0.45% solids, degassed and poured into trays to a depth of 3 mm. The mixture is rapidly frozen and freeze dried. The resultant material is an isomorphic, substantially homogeneous collagen sponge.

EXAMPLE 2

A two-component heteromorphic sponge containing oriented film laminae is prepared as follows:

First, a gel or slurry of fibrous collagen is prepared as described above. Glycerol is added as a plasticiser to a final weight of 0.5% and the gel is then extruded through a suitable flat bed, slit extruder onto a moving belt of suitable material so as to form a fine, unbroken film on the conveyor. The moving conveyor belt passes through a drying cabinet with the temperature set at 55° C. The dry film is stored by rolling onto tube carriers or as pre-cut lengths stored flat in boxes.

In a variant, the films are made by pouring the slurry of collagen onto flat trays and drying in a stream of warm air.

The two-component heteromorphic sponge system is made by fabricating pre-cast and dried films with sponge premix, as follows. A layer of collagen sponge gel or slurry is poured at a thickness of 1 mm and blast frozen. Collagen film is then placed onto the frozen slurry and a second layer of collagen slurry poured to a required thickness. This composite is then blast frozen. Collagen slurry and film layers can be built up to any desired thickness by this procedure. It is also possible, but less convenient, to layer collagen film onto unfrozen collagen slurry followed by a second layer of unfrozen collagen slurry.

In a variant, oxidised regenerated cellulose is obtained commercially in the form of Surgicel™ fabric and is pre-coated with hyaluronic acid (1% solution in water) and re-dried in warm air. This material is used as the uppermost lamina in a sponge film laminated structure made as described above. An advantage of this material is found to be that it can be sutured into place in the wound bed, the Surgicel™ providing strength to hold the sutures.

The degree of orientation of the substructure is determined by scanning electron microscopy (SEM) at 100× magnification of the sponge material sectioned at right angles to the plane of substructure orientation. The substructure films are found to be highly oriented, with a standard deviation from the plane of orientation (ten data points) of only 2 degrees.

EXAMPLE 3

A two-component heteromorphic sponge containing oriented flaked film fragments is prepared as follows. Flakes of the film described in Example 2 are made by homogenising dry collagen film in a Waring Blendor three times, each for 30 sec. at high speed. Larger film flakes are prepared by homogenising for shorter time periods. The flakes of film are then quickly dispersed in the collagen sponge gel (or slurry) described in Example 1 and the mixture is poured into trays and freeze dried.

The degree of orientation of the substructure flakes is determined by SEM as described above. The flakes show roughly coplanar orientation with a standard deviation (based on measurements on 10 flakes) of 12 degrees. The orientation of the flakes appears to have taken place spontaneously in the precursor slurry.

EXAMPLE 4

A two-component heteromorphic sponge containing a substructure of oriented fibres is prepared as follows.

Long fibres in the form of collagen sutures (0.5 mm×5 cm) or oxidised regenerated cellulose threads are inserted longitudinally into a collagen slurry (prepared as in Example 1) retained in a glass Pasteur pipette. The pipette is chilled to −30° C. to freeze its contents, and the glass is then removed by breaking. The frozen cylinder of slurry containing the fibre substructure is then freeze dried.

EXAMPLE 5

A three-component heteromorphic sponge is made as follows. Collagen film flakes and fibres are incorporated together into a collagen sponge gel or slurry and heteromorphic sponges are made as described in Examples 3 and 4.

EXAMPLE 6

Cellular invasion into an oriented heteromorphic sponge is investigated as follows.

A heteromorphic sponge containing oriented substructure of collagen film is prepared as in Example 2. Discs of this sponge of thickness 3 mm and diameter 1 cm are implanted subcutaneously via 1.5 cm incisions through the *paniculus carnosus* of male Sprague Dawley rats (200–250 g) and the incision closed by suture. The rats are sacrificed after 3, 7 and 14 days and the implant and surrounding tissue removed for histological examination. The examination shows that inflammatory cells (polymorphonuclear cells and macrophages), and subsequently fibroblasts, have infiltrated the Sponge matrix of the implant by directed migration along the direction of the laminae of the substructure.

The above examples are intended solely by way of illustration. Many other heteromorphic sponge structures falling within the scope of the accompanying claims will be apparent to the skilled reader.

We claim:

1. A bioabsorbable heteromorphic sponge for use in promoting wound healing, comprising a matrix structure of sponge and at least one macroscopic substructure embedded therein, wherein the matrix and the substructure are formed of bioabsorbable materials and the substructure is anisotropic, thereby defining a scaffolding providing channels in preferred directions for cellular and tissue ingrowth into the sponge.

2. The bioabsorbable heteromorphic sponges of claim 1, wherein the substructure is selected from the group consisting of films, flaked or broken films fibres, fibre bundles and mixtures thereof.

3. The bioabsorbable heteromorphic sponge of claim 1, wherein the substructure comprises films or flaked or broken films defining a laminated structure.

4. The bioabsorbable heteromorphic sponge of claim 1, wherein the substructure defines linear channels in the sponge.

5. The bioabsorbable heteromorphic sponge of claim 1, wherein at least 75% of the substructure is oriented within 30 degrees of a mean direction of orientation of the substructure.

6. The bioabsorbable heteromorphic sponge of claim 1, wherein at least 75% of the substructure is oriented within 20 degrees of a mean direction of orientation of the substructure.

7. The bioabsorbable heteromorphic sponge of claim 1, further comprising a therapeutically effective amount of at least one material which is active in aiding wound healing.

8. The bioabsorbable heteromorphic sponge of claim 1 wherein the matrix structure and at least one substructure have different chemical compositions.

9. The bioabsorbable heteromorphic sponge of claim 1 wherein the material of the matrix structure is the same as the material of the substructure.

10. The bioabsorbable heteromorphic sponge of claim 1 wherein the material of the matrix structure is different from the material of the substructure.

11. The bioabsorbable heteromorphic sponge of claim 10 wherein the material of the matrix structure comprises collagen.

12. The bioabsorbable heteromorphic sponge of claim 1 wherein the material of the matrix structure and the material of the substructure comprises collagen.

13. The bioabsorbable heteromorphic sponge of claim 1 wherein the substructure comprises planar films which provide a plurality of planes for cellular or tissue ingrowth.

14. The bioabsorbable heteromorphic sponge of claim 1 wherein the substructure comprises flaked or broken films which provide a plurality of planes for cellular or tissue ingrowth.

15. The bioabsorbable heteromorphic sponge of claim 1 wherein the bioabsorbable materials of the matrix structure and substructure are chosen from the group consisting of: collagen, elastin, fibronectin, laminim, tenascin, hyaluronic acid, chondroitin sulphate, dermatan sulphate, fibrin, dextran, heparin sulphate, vitronectin, oxidized regenerated cellulose and mixtures thereof.

* * * * *